Feb. 12, 1957 E. S. BOERNER Plant Pat. 1,563
ROSE PLANT
Filed April 23, 1956
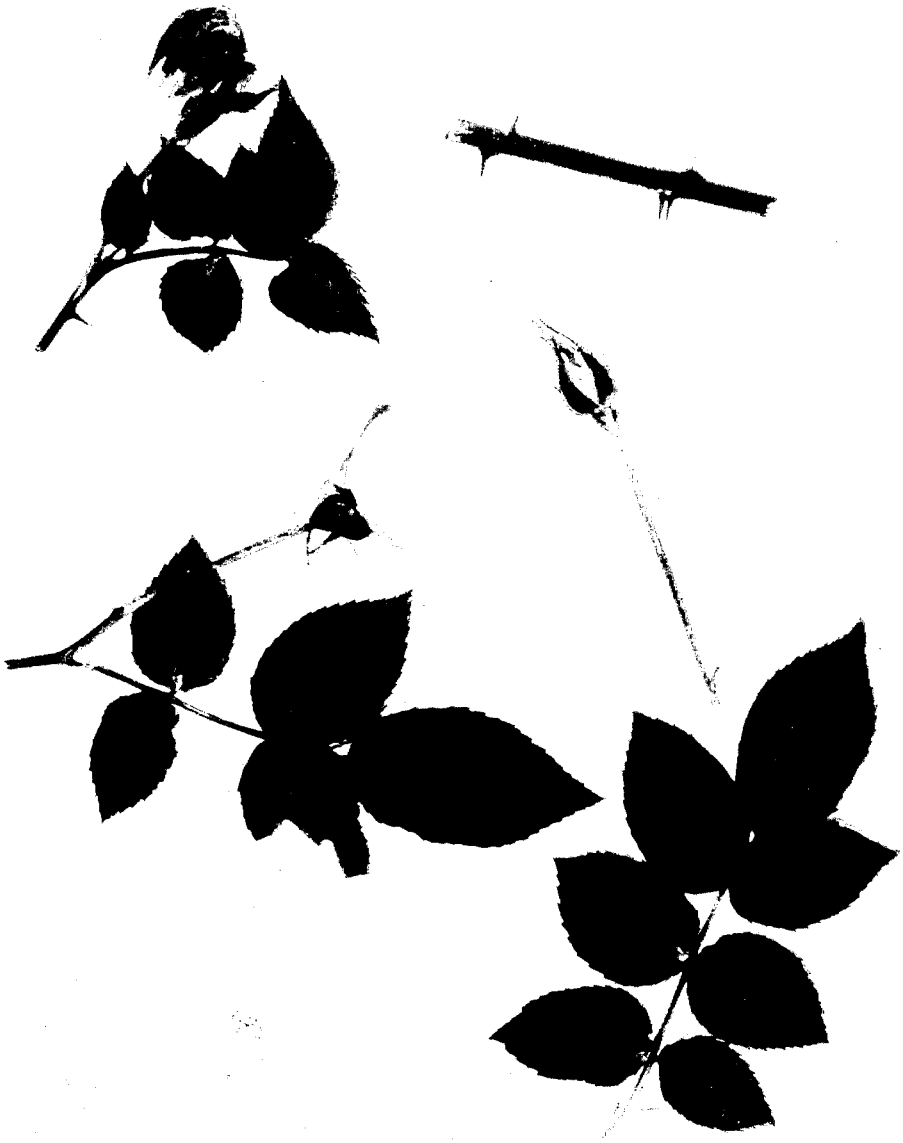
Inventor.
E. S. Boerner
By: Robb & Robb
Attorneys.

United States Patent Office

Plant Pat. 1,563
Patented Feb. 12, 1957

1,563

ROSE PLANT

Eugene S. Boerner, Newark, N. Y., assignor to Jackson & Perkins Company, Newark, N. Y., a corporation of New York Application April 23, 1956, Serial No. 580,150

1 Claim. (Cl. 47—61)

The present invention relates to a new and distinct variety of rose plant of the large-flowered polyantha class, which was originated by me by crossing the variety "Goldilocks" (Plant Patent No. 672) with the variety "Fashion" (Plant Patent No. 789).

The primary objective in making this cross was to produce a new rose variety which combines a flower color other than the usual yellow color of the flowers of "Goldilocks" with a plant habit and type like that of the latter. This objective was fully achieved, along with other improvements and advantages, as evidenced by the following unique combination of features which are outstanding in my new variety:

(1) Prolific flower production and good growing qualities which are achieved both out-of-doors and in the greenhouse;

(2) The graceful and excellent form of the buds, which range from pointed to ovoid in shape;

(3) The slow-opening habit of the buds;

(4) The long-lasting quality of the buds and open flowers; and (5) The distinctive Eosine Pink general color tonality of the flowers, and the retention of such color throughout all stages of development, said color being generally similar to that of the parent variety "Fashion" and being inherited from the latter.

Asexual reproduction of my new variety by budding, as performed at Newark, New York, and also at Pleasanton, California, shows that the foregoing characteristics and distinctions of my new variety come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Goldilocks."
*Pollen parent.*—"Fashion."

Classification:
*Botanic.*—Large-flowered polyantha.
*Commercial.*—Floribunda.

*Flower*

(Observations made from specimens grown in a greenhouse at Newark, New York, in the early morning and near the middle of April.)

Blooming habit: Recurrent—continuous.

Bud:
*Size.*—Medium.
*Form.*—From pointed to ovoid; is not affected by wet or hot weather.
*Color.*—When sepals first divide—Eugenia Red, Plate 13. When petals begin to unfurl—Eosine Pink, Plate 1. When half-blown: inside of petals—Eosine Pink, Plate 1, lightly overcast with Thulite Pink, Plate 26; reverse of petals—Thulite Pink, Plate 26, lightly overcast with Eosine Pink, Plate 1.
*Sepals.*—Slightly branched; with "hood" above bud; curl back when petals begin to unfurl. Color: inside—Kildare Green, Plate 31; outside—Biscay Green, Plate 17.
*Calyx.*—Color—Biscay Green, Plate 17. Shape—pear. Size—slender. Aspect—smooth. Odor when rubbed—none.
*Peduncle.* — Length — medium. Aspect — rough. Strength—stiff; slender. Color—Parrott Green, Plate 6.
*Opening.*—Opens up well; is not affected by adverse weather conditions.

Bloom:
*Size.*—Medium. Average size when fully expanded—3 inches.
*Borne.*—Several together and in irregular clusters.
*Stems.*—Medium length; normal strength.
*Form (when first open).*—Cupped. Permanence—flattens.
*Petalage.*—Double (full but open center). Number of petals under normal conditions—from 35 to 40.
*Color.*—Center of flower—La France Pink, Plate 1, lightly overcast with Eosine Pink, Plate 1, with lower half of the petal lightly overcast with Orange Buff, Plate 3. Outer petals—Thulite Pink, Plate 26, lightly overcast with La France Pink, Plate 1. Base of petals (aiglet)—Pale Green Yellow, Plate 5. Inside of petals—La France Pink, Plate 1, lightly overcast with Thulite Pink, Plate 26. Reverse of petals—Cameo Pink, Plate 26. General tonality from a distance—Eosine Pink, Plate 1.
*Discoloration.*—General tonality at end of first day—La France Pink, Plate 1, lightly overcast with Eosine Pink, Plate 1. Second day—La France Pink, Plate 1, lightly overcast with Thulite Pink, Plate 26. Third day—La France Pink, Plate 1, overcast with Cameo Pink, Plate 26.

Petals:
*Texture.*—Leathery; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—very long. As cut flower—very long.

*Genital organs*

Stamens, anthers: Medium size; many; regularly arranged around styles. Color—Light Orange Yellow, Plate 3.
Stamens, filaments (threads): Short. Color—Picric Yellow, Plate 4.
Pollen: Color—Pale Orange Yellow, Plate 3.
Styles: Columnar; uneven length; medium length; thin.
Stigmas: Color—Chalcedony Yellow, Plate 17.
Ovaries: All enclosed in calyx.
Hips: None.
Seeds: None.

*Plant*

Form: Bush.
Growth: Vigorous; upright.
Foliage: Compound of 5 to 7 leaflets.

*Size.*—Medium.

*Quantity.*—Normal.

*Color.*—New foliage: upper side—Grass Green, Plate 6, with edges of leaves and serrations Oxblood Red, Plate 1; under side—Mahogany Red, Plate 2, with center of leaf Parrott Green, Plate 6. Old foliage: upper side—Deep Dull Yellow Green, Plate 32; under side—Turtle Green, Plate 32, lightly overcast with Oxblood Red, Plate 1.

*Shape.*—Oval pointed.

*Texture.*—Upper side—glossy. Under side—smooth.

*Ribs and veins.*—Prominent.

*Edge.*—Serrated (saw-toothed).

*Serration.*—Both double and single; deep.

*Leaf stem.*—Color—Light Hellebore Green, Plate 17, lightly overcast with Hay's Russett, Plate 14. Under side—prickly.

*Stipules.*—Short; smooth.

Wood:

*New wood.*—Color—Courge Green, Plate 17. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; straight. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its good growing qualities and prolific flower production, both outdoors and in the greenhouse, the graceful and excellent form of its buds which range from pointed to ovoid in shape, the slow-opening habit of its buds, the long-lasting quality of its open flowers, and the Eosine Pink general color tonality of its flowers and the retention of such color throughout all stages of development of the flowers.

No references cited.